United States Patent [19]

Niesel et al.

[11] Patent Number: 5,356,797
[45] Date of Patent: Oct. 18, 1994

[54] MEMBRANE EXPRESSION OF HETEROLOGOUS GENES

[75] Inventors: David W. Niesel, League City; J. Scott Moncrief; Linda H. Phillips, both of Galveston, all of Tex.

[73] Assignee: Board of Regents, The University of Texas, Austin, Tex.

[21] Appl. No.: 792,525

[22] Filed: Nov. 15, 1991

[51] Int. Cl.$^5$ .................. C12N 1/21; C12N 15/30; C12N 15/70; C12N 15/74
[52] U.S. Cl. ................. 435/69.3; 435/67.1; 435/172.1; 435/172.3; 435/252.3; 435/320.1; 536/23.1; 536/23.7; 536/24.3
[58] Field of Search ............ 435/69.1, 69.3, 320.1, 435/172.3, 252.3, 252.8; 536/27, 23.7, 23.1, 24.3

[56] References Cited

U.S. PATENT DOCUMENTS 4,914,025  4/1990  Manoil et al. ................. 435/69.8

FOREIGN PATENT DOCUMENTS 0251579  1/1988  European Pat. Off. .
0355737  2/1990  European Pat. Off. .
0368819  5/1990  European Pat. Off. .
0407259  1/1991  European Pat. Off. .
3901681  7/1990  Fed. Rep. of Germany .

OTHER PUBLICATIONS

Breitling et al., "A Surface Expression Vector for Antibody Screening," *Gene*, 104:147-153, 1991.
Manoil and Beckwith, "TnphoA: A Transposon Probe for Protein Export Signals," *Proc. Natl. Acad. Sci. USA*, 82:8129-8133, 1985.
Moncrief et al., "Surface Expression of a PhoA Fusion Protein from an Invasion-Attenuated *Salmonella typhimurium*," *Abstr. Gen. Meet. Am. Soc. Microbiol.*, 91 (1991) Abstract No. B55.
Stokes and Hall, "A Novel Family of Potentially Mobile DNA Elements Encoding Site-Specific Gene-Integration Functions: Integrons," *Mol. Microbiol.*, 3(12):1669-1683, 1989.
Phillips et al., "*Salmonella* Exposition Vectors Derived from Tn*phoA* Fusion Strains," *Abstr. Gen Meet. Am. Soc. Microbiol.*, 92, (1992) Abstract No. H-256.
Galán et al., Gene, 94(1):29-35, 1990.
Sukupolvi et al., Mol. Microbiol., 4(1):49-57, 1990.
Yan et al., Res. Microbiol., 141:1003-1004, 1990.
Sanchez et al., Res. Microbiol., 141:971-979, 1990.
Sory & Cornelis, Res. Microbiol., 141:921-929, 1990.
Manoil et al., J. Bacteriol., 172(2):515-518, 1990.
Strugnell et al., Gene, 88:57-63, 1990.
Müller et al., J. Bacteriol, 171(9):4648-4654, 1989.
Miller et al., Infect. Immun., 57(9):2758-2763, 1989.
Smith et al., J. Bacteriol., 169(7):3321-3328, 1987.
Wright et al., J. Cell. Biochem., 346, Supp. 7B, Abstract #1408.

*Primary Examiner*—Richard A. Schwartz
*Assistant Examiner*—David Guzo
*Attorney, Agent, or Firm*—Arnold, White & Durkee

[57] ABSTRACT

The invention relates to nucleic acid segments useful in the construction of expression vectors for expression of heterologous polypeptides directed to particular areas of the host cell. Selected constructs direct production of polypeptides to the outer membrane surface of the cell. Other constructs direct expression of heterologous polypeptides to the inner membrane/periplasm of the host cell. Transformed host cells are potentially useful for the production of vaccines or immunogens elicited in response to antigens expressed on the outer membranes of the host cells.

24 Claims, 11 Drawing Sheets

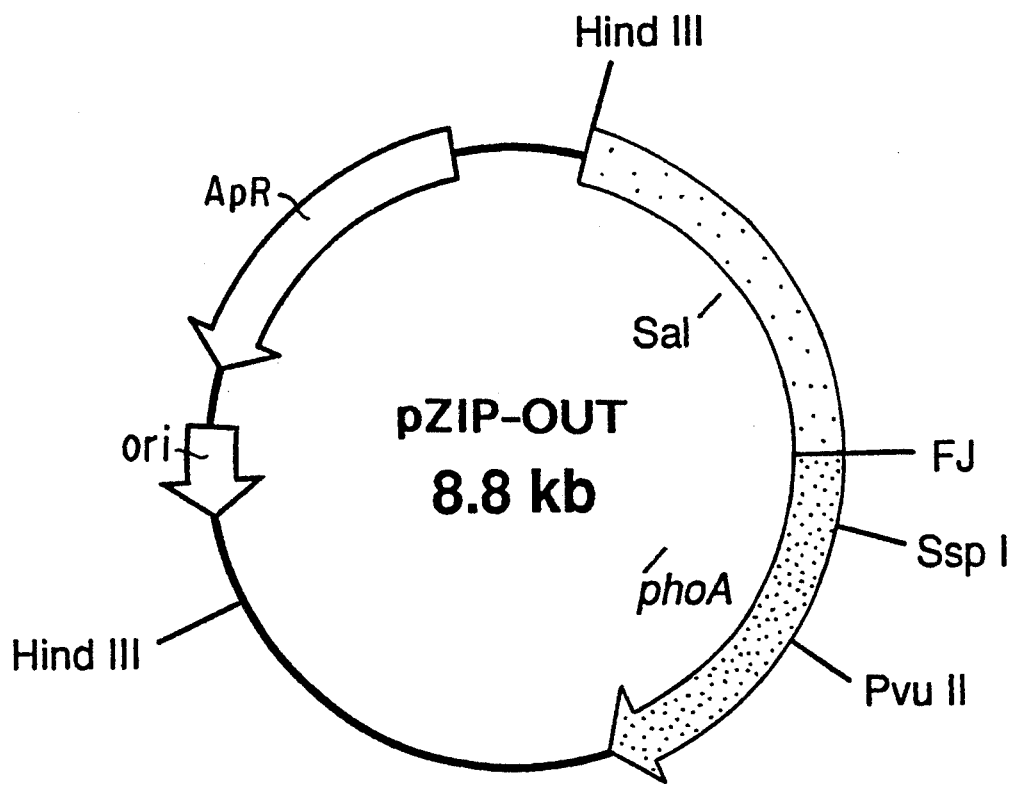

FIG. 2A

-353
5'- AAATCCTG//GAAACCGATTCGCCCCCT<u>TATAAC</u>TATTGTCAGATA

ACGTTCTGACGGTTGTGTAAAAACATGGCGCCTCATTCTTCTGTAGTTGGAGTTAAT

| met | | lys | | tyr | | cys | | pro | | phe | | *leu* | | gly |
|---|---|---|---|---|---|---|---|---|---|---|---|---|---|---|
| | lys | | phe | | ser | | leu | | val | | leu | | *ile* | |

ATG AAA AAA TTT TAT AGC TGT CTT CCT GTC TTT TTA CTG ATC GGC

| *cys* | | pro | | ser | | thr | | val | | ser | | thr |
|---|---|---|---|---|---|---|---|---|---|---|---|---|
| | ala | | asp | | tyr | | gln | | ala | | trp | | glu |

TGT GCT|CCT GAC TCT TAT ACA CAA GTA GCG TCC TGG ACG GAA
————IS50L————————————————

| pro | | pro | | cys | | val | | glu | | arg |
|---|---|---|---|---|---|---|---|---|---|---|
| | phe | | phe | | pro | | leu | | asn | |

CCT TTC CCG TTT TGC|CCT GTT CTG GAA AAC CGG  //  -3'
————————————phoA————————

FIG. 2B

5'- GCGTGCA<u>TAATAA</u>GCCCTACACAAATT<u>GGGAG</u>ATATATC ATG AAA GGC TGG →

CTT TTT CTT GTT ATC GCA ATA GTT GGC GAA GTA ATC GCA ACA TCC

GCA TTA AAA TCT AGC GAG GGC TTT ACT AAG CTT GCC CCT TCC GCC

GTT GTC ATA ATC GGT TAT GGC ATC GCA TTT TAT TTT CTT TCT CTG

GTT CTG AAA TCC ATC CCT GTC GGT GTT GCT TAT GCA GTC TGG TCG

GGA CTC GGC GTC GTC ATA ATT ACA GCC ATT GCC TGG TTG CTT CAT

GGG CAA AAG CTT GAT GCG TGG GGC TTT GTA GGT ATG GGG CTC ATA

GCT GAC TCT TAT ACA CAA GAT GCG CCT GTG ACG GAA CCT TTC CCG
└─────────────────────────IS50L─────────────────────────

TTT GAC┐ ┌CCT GTT CTG GAA ACC  -3'
└──────┘└── phoA ──

FIG. 11

MEMBRANE EXPRESSION OF HETEROLOGOUS GENES

The United States Government may have certain rights in the present invention pursuant to Grant No. R29 AI24677 awarded by the National Institutes of Health.

BACKGROUND OF THE INVENTION

1. Field of the Invention

The invention relates generally to the exportation of heterologous polypeptides to discrete regions of a host cell in which it is expressed, to nucleic acid sequences encoding exportation polypeptides, to the preparation of membrane embedded epitopes of immunogenic antigens, and to vectors constructed with selected exportation sequences. More particularly, localized expression of polypeptides may be obtained by providing exportation signals encoded by segments of the disclosed nucleic acids that provide for exportation of expressed heterologous polypeptides to the inner membrane/periplasmic space or the outer membrane surface of a host cell.

2. Description of Related Art

Recombinant gene technology has been extensively investigated in the context of expression of foreign proteins in host cells which harbor recombinant genes, typically bacterial host cells. Such expression is desirable for producing high value proteins, immunogenic polypeptides, and in obtaining hybrid proteins that are otherwise difficult to synthesize.

Of particular interest is vaccine development. It is potentially feasible to prepare protective vaccines from epitopes of known antigens of eukaryotic, viral or prokaryotic pathogens by taking advantage of the synthetic capacities of transformed host cells. Examples include tumor specific proteins which might be expressed and utilized to stimulate an immune response. Oral vaccines have stimulated research because of the ease of administration and, more importantly, in some instances the unsatisfactory protection afforded from parenteral injection. Vaccination against cholera, for example, gives short-term protection, thus provoking developmental work toward an oral vaccine that would presumably stimulate mucosal intestinal immunity more efficiently (Sanchez et al., 1990).

Salmonella strains are being studied experimentally as particularly attractive candidates for producing oral live vaccines. Attenuated strains have been shown to elicit immune responses in several animal species (Strugnell et al., 1990) and apparently can be highly immunogenic in the host. Humoral antibody responses including local secretory antibody and cellular immune responses have been observed after oral intake (Dougan et al., 1986). Attenuated mutants have been identified via screening procedures such as TnphoA mutagenesIS, which exclude elimination of mutations in nonsecreted proteins (Miller et al., 1989). However, TnphoA methods only indicate assessment of integration of the transposon into a gene for a secreted or cytoplasmic protein.

Protein expression systems have been developed from Salmonella strains. A cloning vector useful for integrating DNA into the aroC gene on Salmonella chromosomes was used to direct expression of heterologous antigens such as tetanus toxin fragment C and Treponema pallidum lipoprotein (Strugnell et al., 1990). In some cases, heterologous polypeptide gene products orally administered have elicited a serum antibody response, as for example, the cholera toxin B subunit protein expressed from a recombinant Yersinia enterocolitica strain (Sory and Cornelis, 1990). Unfortunately, while antibodies were detected in sera of challenged mice, the response was variable and was directed toward polymeric forms of cholera toxin B.

It is recognized that cytoplasmic proteins may not produce a high immunogenic response and heterologous proteins from recombinant DNA molecules expressed cytoplasmically often exhibit a diminished antibody reactivity (Sanches, Et. Al., 1990). Thus surface expressed epitopes of bacteria are expected generally to elicit the greatest humoral response; however, factors controlling surface expression of heterologous proteins have not been defined and there is no way to assure that any given fusion protein will localize to a host cell membrane surface.

Vaccines are the most cost effective medical intervention known to prevent disease. However, effective vaccines are available for relatively few diseases. Successful immunization against infectious organisms often requires a multicomponent host immune response against a variety of antigenic determinants. Orally administered vaccines, especially live attenuated vaccines, induce specific cell-mediated effector responses and elicit secretory IgA (sIgA) responses. SIgA is important because of its effectiveness at mucosal surfaces. SIgA production and cell effector responses are mediated through the delivery of antigens to gut-associated lymphoid tissue (GALT). Stimulation of GALT can lead to effective cell and humoral defense at all mucosal surfaces and provide systemic protection (1,2).

To deliver antigens to GALT, investigators have developed avirulent and virulence-attenuated Salmonella stains. Aromatic dependent (aroA (3)), phoP (4), galE (5), and cya/crp (6) Salmonella mutants have been reported to interact with GALT in the lamina propria and stimulate an immune response. While it is clearly desirable to use avirulent Salmonella strains as carriers for plasmids which express protective antigens of other pathogens on their surface, it is clear that improvements are needed to develop protective vaccines based on this system.

The use of attenuated Salmonella strains to express heterologous antigens and stimulate GALT is being extensively investigated. In some studies, detectable levels of specific mucosal and serum antibodies to the heterologously expressed antigen have been observed (7–10). However, in general results with most antigens have been variable.

It is generally believed that the export of heterologous epitopes to the Salmonella cell surface enhances their immunogenicity (11). Investigators have used recombinant DNA methods to express heterologous epitopes as inserts in Salmonella flagellin (9) and the lamb encoded polypeptide of E. coli (10). In these studies, a significant antibody response to the heterologous surface-expressed epitopes was observed. A limitation of these systems is the relatively small number of epitopes which can be inserted into the lamb and flagellin genes. This is important as single (or few) epitopes may not result in the broad-based immune response which characterizes today's most successful vaccines.

There is clearly a need to develop effective systems to elicit antibody response and in particular to provide methods of exporting heterologous polypeptides to the surface of appropriate host cells. Antigenic peptides expressed on bacterial host cell surfaces may be significant in developing vaccines to such important antigens as cholera B subunit toxin and HIV antigens.

SUMMARY OF THE INVENTION

The present invention addresses one or more of the foregoing or other problems associated with methods of controlling surface expression of heterologous polypeptides in a host cell and provides in particular a method of directing exported polypeptides to outer cell membrane surfaces or to inner membrane/cytoplasmic regions. The invention includes nucleic acid segments useful for preparing expression vectors. Such vectors are suitable for expressing and directing heterologous polypeptides exported to selected areas of the host cell. Transformed cells with surface expressed antigens or epitopic regions are expected to be useful as immunogens producing an effective immune response.

The nucleic acid segments of the present invention encode amino acid sequences associated with particular targeting of fused heterologous polypeptides to particular areas of a transformed host cell. It has been found for example that nucleic acid segments defined by SEQ ID NO:1 encode a polypeptide product which when fused to a heterologous polypeptide will direct that polypeptide to the outer membrane of a bacterial cell. By heterologous polypeptide is meant any polypeptide other than those normally associated SEQ ID NO:1. It is of course understood that such localizing capabilities are realized under conditions when the exportation polypeptide is incorporated into a suitable expression vector and an appropriate cell host is transformed with that vector. A preferred embodiment of the DNA segment is defined by SEQ ID NO:1. This sequence fused to a phoA sequence encodes a 46 Kda polypeptide.

The present invention also includes nucleic acid segments encoding amino acid sequences associated with the transport of heterologous polypeptides to the bacterial inner membrane periplasmic space. Particular embodiments of these sequences are included in the nucleic acid sequences defined in SEQ ID NO:2. A preferred inner membrane periplasmic space directing polypeptide is a 55 Kda polypeptide encoded by the gene sequence illustrated in FIG. 3 and defined in SEQ ID NO:2. This preferred embodiment includes gene sequences encoding part of the alkaline phosphatase gene, however, other heterologous genes could be used in place of alkaline phosphatase.

While particular nucleic acid sequences have been defined it is nevertheless contemplated that nucleic acid sequences will be found to vary. It is expected that analogous sequences with similar functions may be found in other gram-negative bacteria such as $E.$ $coli.$ In certain particular embodiments, the invention concerns expression vectors that are constructed to include any of the DNA segments herein disclosed. Such DNA may be fused directly with a gene of interest and used in an expression system to produce heterologous polypeptides as hybridization probes for, e.g., identifying related sequences, as primers or even as building blocks for the construction of mutant or variant sequences. A particularly useful application of the DNA segments of this invention is to achieve directed expression of heterologous polypeptides. Depending on the DNA segment selected, polypeptides will be expressed on the inner membrane periplasmic space, the outer membrane of the host cell, or on the surface of the outer membrane of the host cell.

In particular embodiments, the pZIP plasmids of FIG. 2 and FIG. 3 have been constructed. Depending on the plasmid selected, fusion polypeptides are exported to the inner membrane/periplasmic space or to the outer membrane of the host cell. In a preferred embodiment, pZIP-OUT directs the export of fusion polypeptides to the outer membrane and may also direct a heterologous peptide to the external surface of a gram-negative host cell. pZIP-OUT is a vector which expresses bipartite fusion which includes a DNA segment capable of exporting the fusion product to the external membrane of a gram-negative cell. The other part of the chimeric gene is a phoA gene segment lacking signal and expression segments. A variety DNA segments may be inserted into the phoA segment at suitable restriction sites to create a tripartite fusion.

Yet another preferred embodiment is the pZIP-IN plasmid shown in FIG. 3. This plasmid directs the export of polypeptides to the inner membrane periplasmic space. The construction of the plasmid is bipartite. Part of the alkaline phosphatase gene lacking signal and expression sequences is fused with a DNA sequence that contains an exportation sequence capable of directing its fusion polypeptide to an inner membrane/periplasmic space. There are several restriction sites in the phoA gene segment into which foreign DNA or fragments of DNA may be inserted.

Other components of either of these plasmids may include, in addition to the export specifying sequences, resistance genes such as ampicillin or tetracycline resistance genes. In addition an $E.$ $coli$ phoA gene may be fused in frame with expression directing DNA sequences, such as that used to construct the pZIP-IN and pZIP-OUT plasmids. pZIP-IN additionally encodes a kanamycin resistance gene. An advantage of using the phoA fusion is that there are various restriction sites within the phoA gene facilitating the fusion of heterologous gene sequences in frame with phoA and the export specifying sequences.

Expression vectors may also include a gene encoding a detectable polypeptide. Typical examples of reporter genes encoding detectable polypeptides include β-lactamase and alkaline phosphatase genes. Reporter genes may be conveniently fused inframe downstream of the disclosed nucleic acid sequences with or without other DNA fragments/segments. Moreover, restriction sites in the gene sequence of the reporter gene may be used for insertion of a desired DNA fragment(s).

Recombinant vectors such as those described are particularly preferred for transforming bacterial host cells. Several types of bacterial host cells may be employed, most preferred being gram-negative cells such as $E.$ $coli$, Salmonella and the like.

Transformed cells may be selected using various techniques including screening by differential hybridization, identification of fused reporter gene products, resistance markers, anti-antigen antibodies, and the like. After identification of an appropriate clone it may be selected and cultivated under conditions appropriate to the circumstances, as for example, conditions favoring expression.

Another aspect of the invention is a method of preparing heterologous polypeptides. The method generally involves preparing one or more of the recombinant vectors herein disclosed, transforming a host cell with the recombinant vector, then selecting a vector containing host cell clone and finally isolating from the clone the desired polypeptide which will be a heterologous protein. Examples of useful proteins that might be used in preparing the recombinant vector include alkaline phosphatase, cholera toxin B subunit, fragments of these proteins, or any other desired proteins.

Depending on the particular recombinant vector selected for transforming a host cell, recombinant heterologous polypeptides will be expressed in different compartments of the cell. For those heterologous polypeptides expressed in the inner membrane or periplasmic space isolation of the heterologous polypeptide may be affected by cell lysis and other procedures utilized in the isolation of a desired fusion protein. Heterologous fusion proteins exported to the outer membrane of the host cell may be isolated from the outer membrane directly Typical procedures include separation of inner and outer cell membranes and then isolation of the fusion peptide from membranous material.

In a preferred embodiment, antigenic proteins are expressed on the surface of the host cell. Selected epitopes of eukaryotic viral or prokaryotic pathogens expressed on the surface of a host cell may be used for vaccine development. Tumor specific genes could be expressed and utilized to stimulate an immune response. Whole cells expressing immunogenic epitopes might be used for agglutination-based screening tests. Surface expressed polypeptides of other organisms might be identified by screening recombinant libraries for specific surface expressed polypeptides. In another preferred embodiment, cholera toxin B subunit may be expressed on the surface of a Salmonella harboring the pZIP-OUT plasmid vector hereinabove described. When expressed from Salmonella strain TA2362 harboring plasmid PRSP18, chorlera toxin B subunits agglutinated in the presence of specific antibody, indicating exposure of epitopic regions on the external membrane surface of formalin-fixed cells.

Another aspect of the invention involves the preparation of vaccines. Antigens or epitope(s) are selected and a gene encoding these moieties is inserted into one or more of the recombinant vectors disclosed. Appropriate host cells are transformed and after screening for transformants one is selected which expresses the antigen or epitopes for which a vaccine is desired. Vaccines may then be prepared by a variety of methods. Antigens on the surface of appropriate host cells may be safely administered orally. For example, attenuated Salmonella orally administered could stimulate an immune response on gut mucosa. Alternatively, whole cells or cell fragments containing the membrane-bound antigen may be suitably injected into a mammal to generate an immune response. In any event, it is expected that the immunogenicity of an antigen or epitope may be significantly enhanced when expressed on the surface of a bacterial cell.

In both immunodiagnostics and vaccine preparation, it is often possible and indeed more practical to prepare antigens from segments of a known immunogenic protein or polypeptide. Certain epitopic regions may be used to produce responses similar to those produced by the entire antigenic polypeptide. Often however responses to epitopic regions are not so strong as responses to the entire polypeptide. However, surface expression of these epitopes may generate an enhanced immune response.

In other embodiments, the invention concerns primers capable of priming amplification of selected portions of disclosed DNA segments. Primers hybridize to DNA and serve as initiation sites for synthesis of a portion of the gene. Nucleotide primers are designed to bind at separate sites on opposing duplex strains thereby defining the intervening sequence as the portion to be amplified. Nucleic acid molecules to be employed as primers whether DNA or RNA will generally includes at least a 10 nucleotide segment of the nucleic acid sequence of SEQ ID NO:1 or SEQ ID NO:2. The 10 base pair size is selected as a general lower limit in that sizes smaller than 10 bases hybridization stabilization may be become a problem. However, as the size of the primer decreases too much below 7-8 bases, non-specific hybridization may occur with other genes having complimentary sequences over short stretches.

Primers may be utilized for several purposes. For example, primers may be used to amplify selected portions of the disclosed DNA segments. Certain primer combinations may more efficiently generate DNA encoding polypeptides that more effectively target to inner or outer membranes. Additionally, primers prepared from the disclosed DNA may be used to amplify regions of DNA from other related organisms in order to identify similar targeting sequences. Once amplified products are obtained probes which referred to nucleic acid molecules employed to detect DNA sequences through hybridization procedures may be employed to detect and isolate selected DNA fragments. Like primers, probes may be DNA or RNA and are generally of similar size usually including at least a 10 nucleotide segment or more, often of 220 or 21 base pairs. Probes may be labeled, for example, by radio labeling, to assist in identification of nucleic acid sequences.

As part of the invention, kits useful for the expression of fusion proteins are also envisioned comprising separate containers, each having suitably aliquoted reagents for performing the foregoing methods. For example, the containers may include one or more vectors, examples being the vectors of claim 19, particular embodiments of which are shown schematically in FIGS. 4 and 5. Suitable containers might be vials made of plastic or glass, various tubes such as test tubes, metal cylinders, ceramic cups or the like. Containers may be prepared with a wide range of suitable aliquots, depending on applications and on the scale of the preparation. Generally this will be an amount that is conveniently handled so as to minimize handling and subsequent volumetric manipulations. Most practitioners will prefer to select suitable endonucleases from common supplies usually on hand; however, such restriction endonucleases could also be optionally included in a kit preparation.

Vectors supplied in kit form are preferably supplied in lyophilized form, although such DNA fragments may also be taken up in a suitable solvent such as ethanol, glycols or the like and supplied as suspensions. For most applications, it would be desirable to remove the solvent which for ethanol, for example, is a relatively simple matter of evaporation.

BRIEF DESCRIPTION OF THE DRAWINGS

FIG. 2 shows the DNA sequence across the Salmonella::phoA fusion joint in pZIP-OUT. Dideoxy sequencing (Sequenase 2.0 USB Biochemicals) was used to determine the 353 base pairs (bp) upstream of the Salmonella::phoA fusion joint. A single open reading frame (ORF) which was in frame with that of the IS50L/phoA sequence was observed. A stop codon in this ORF was observed at position −99. Multiple stop codons in all reading frames were present in sequences −150 to −200. Two putative translation start codons (AUG) were present at positions −84 and −51. A putative Pribnow box (=) was present at position −120. The predicted amino acid sequence (SEQ ID NO:3) of the coding region is shown above the nucleotide sequence (SEQ ID NO:1). The IS50L and the beginning of the phoA derived sequences are underlined.

FIG. 2 also schematically shows that plasmid pZIP-OUT contains a 4.5K6 HindIII chromosomal fragment from invasion-attenuated *S. typhimurium* TnphoA insertion mutant TAP 43 inserted into pBR322 at the HindIII site. It expresses a 46 Kd PHOA fusion protein which localizes to the outer membrane.

FIG. 11 shows the sequence of export specific signal in pZIP-IN. Promoter and regulatory sequences are underlined. IS50L and phoA sequences from pZIP-IN are shown. The ORF is shown in capital letters. The complete nucleic acid sequence is represented by SEQ ID NO:2

DETAILED DESCRIPTION OF THE PREFERRED EMBODIMENTS

Figure 1:
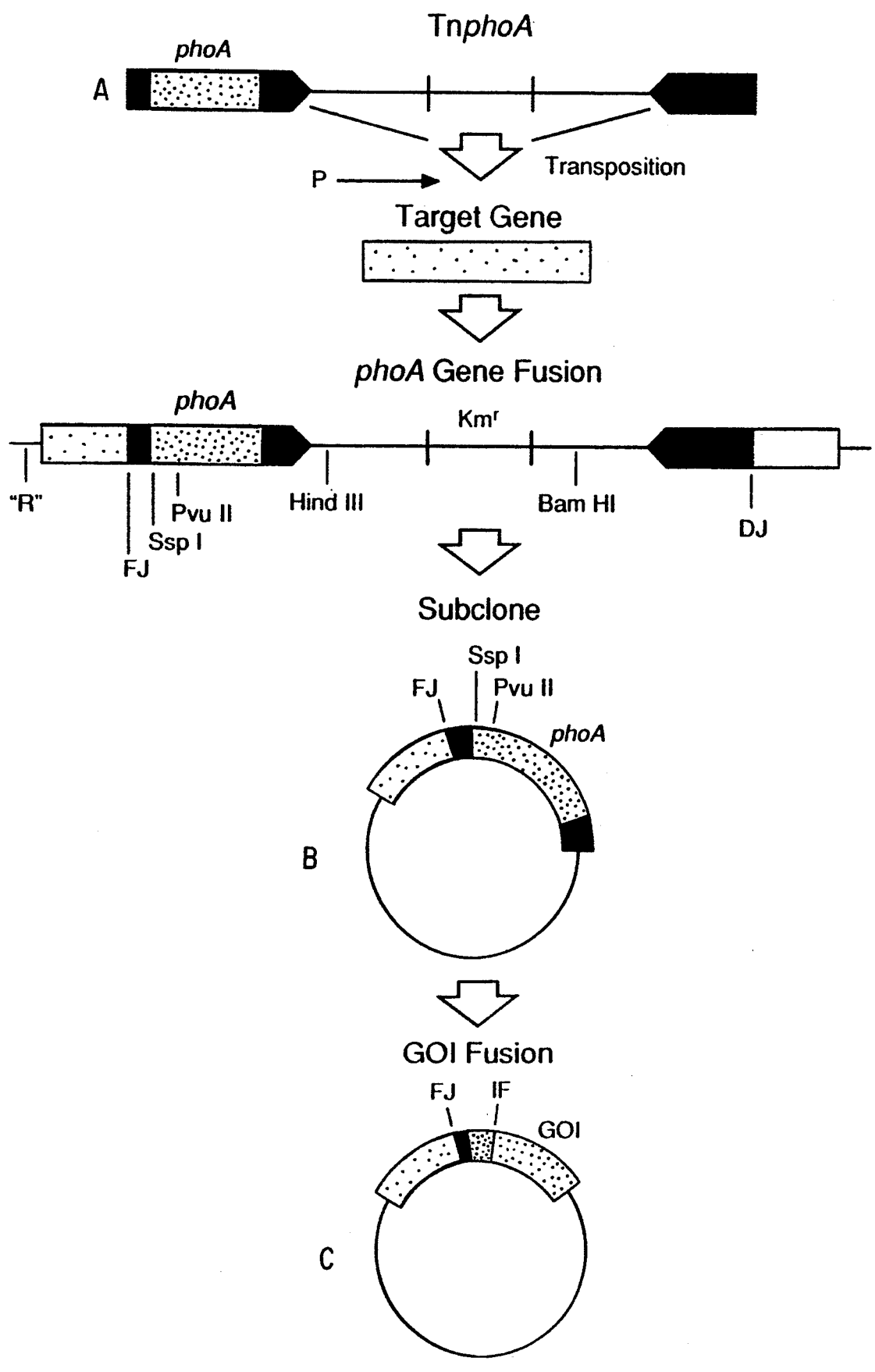
FIG. 1 illustrates the cloning of phoA gene fusion from TnphoA insertion mutants and construction of tribrid gene fusions. TnphoA is a derivative of Tn5 which encodes E. coli alkaline phosphatase, minus the signal sequence and expression signals, inserted into the left IS50L element (21). Random transposition of TnphoA results in an active insertion only when the phoA gene sequence is fused in frame downstream of the promoter and export signals of a target gene (A). The point at which the phoA sequence joins the target gene is referred to as the fusion joint (FJ). The remaining portion of the gene begins at the distal joint (DJ). Utilizing restriction enzymes which cut either downstream of the kanamycin resistance gene (e.g., BamHI) or the phoA gene sequence (e.g., HindIII), allows cloning of phoA gene fusions (if the target gene is not also restricted ("R")). Plasmids carrying phoA gene fusions can then be used as exposition vectors (B). The SspI and PvuII restriction sites in phoA provide blunt ended sites at which in frame insertions (IF) of a gene of interest (GOI) can be inserted. The GOI must also be consistent with the phoA frame at the insertion site. The resulting tribrid gene fusions contain the expression and export signals of the target gene fused in frame with the phoA and GOI sequences.

The present invention relates to nucleic acid segments encoding particular polypeptides capable of forming fusion proteins that export to particular areas of a host cell. These nucleic acid segments are useful in constructing vectors that allow expression of heterologous proteins in appropriately transformed host cells. Polypeptides may be localized within the inner membrane/periplasmic space or on the outer membrane surface. Antigens or epitopic regions of antigens localized on host cell membranes have particular potential for vaccine development and antibody production.

A heterologous gene expression system has been developed which utilizes a virulence-attenuated Salmonella as a carrier for a plasmid expression system (pZIP-OUT) which can direct the products of large segments of heterologous genes to the outer membrane (FIG. 2). Recombinant DNA techniques are utilized to fuse the reading frame of the gene to be expressed with Salmonella export specifying sequences, FIG. 1. Several cloning sites are possible which allow maintenance of the proper reading frame and produce tribrid fusion polypeptides which contain Salmonella export specifying sequences, the heterologous gene sequences and phoA gene sequences. Recombinants which export the tribrid fusion protein are selected through the loss of phoA activity and appearance of the predicted fusion polypeptide on the surface of the outer membrane. A tribrid fusion has been constructed which encodes virtually the entire cholera toxin B subunit (ctxB) gene, FIG. 6, and evaluated its subcellular localization in Salmonella. This fusion polypeptide is expressed on the Salmonella surface as evidenced by: 1) agglutination of tribrid fusion expressing strains by anti-CTB antiserum, 2) localization of the fusion polypeptide in the outer membrane, and 3) the presence of the fusion polypeptide in cell surface preparations.

The DNA of the present invention was isolated from *Salmonella typhimurium*, strain TAP43, an invasion attenuated strain. Invasion attenuated refers to species which have lost one or more virulence factors affecting the efficiency by which Salmonella invades epithelial cells. Isolation of an attenuated strain of Salmonella was considered useful in developing the present invention because such strains may be used to deliver heterologous antigens to the gut of an animal. Salmonella given orally tends to establish an infection in the intestinal mucosa, leading to an immune response. The presence of a desired antigen is expected to stimulate a response to that species, as well as to the Salmonella or other host antigens.

The approach to screening for protein export signals was to use alkaline phosphatase fusions based on the TnphoA transposon system reviewed by Manoil et al. (1990). TnphoA is a transposon derivative of Tn5 in the phoA gene which lacks a promoter, translation initiation site, signal sequence DNA and the first five amino acids of its protein. When the transposon, TnphoA, inserts into a foreign gene in the correct orientation and reading frame, gene fusions are generated, coding for hybrid proteins which have alkaline phosphatase activity if transported beyond the inner member. Detection of such activity is generally accomplished with an alkaline phosphatase indicator dye, allowing visualization of colored colonies for successful gene fusions that lead to export of heterologous gene products.

Part of the present invention contemplates vaccine preparation and use. In general, it is contemplated that antigens, or epitopes of antigens, will be readily expressed in localized regions of a host cell using the methods disclosed. Expression vectors incorporating the DNA segment encoding exportation polypeptides directing products to a host cell outer membrane surface are expected to be particularly useful. Epitopic regions of antigens, well exposed at a membrane surface, may elicit high immunogenic responses, providing a route to vaccines or antibody production.

General concepts related to methods of vaccine preparation and use are discussed as applicable to preparations and formulations with antigens, epitopes or subfragments of such antigens obtained from various sources; for example, cholera B toxin subunit and the like.

Vaccine Preparation and Use

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with a 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be administered from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

The invention also contemplates the use of disclosed nucleic acid segments in the construction of expression vectors or plasmids and use in host cells. The following is a general discussion relating to such use and the particular considerations in practicing this aspect of the invention.

Host Cell Cultures and Vectors

In general, of course, prokaryotes are preferred for the initial cloning of DNA sequences and constructing the vectors useful in the invention. For example, in addition to the particular strains mentioned in the more specific disclosure below, one may mention by way of example, strains such as *E. coli* K12 strain 294 (ATCC No. 31446), *E. coli* B, and *E. coli* X 1776 (ATCC No. 31537). These examples are, of course, intended to be illustrative rather than limiting.

Other prokanyotes may also be preferred for expression. The aforementioned strains, as well as *E. coli* W3110 (F-, lambda-,prototrophic, ATCC No. 273325), bacilli such as *Bacillus subtilus*, or other enterobacteriaceae such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an E. coli species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the β-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally into plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used. *Saccharomyces cerevisiae*, or common baker's yeast is the most commonly used among eukaryotic microorganisms, although a number of other strains are available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Also contemplated within the scope of the present invention is the use of the disclosed DNA as a hybridization probe. While particular examples are provided to illustrate such use, the following provides general background for hybridization applications taking advantage of the disclosed nucleic acid sequences of the invention.

Nucleic Acid Hybridization Embodiments

In certain aspects, the DNA sequence information provided by the invention allows for the preparation of relatively short DNA (or RNA) sequences having the ability to specifically hybridize to *S. typhimurium* gene sequences. In these aspects, nucleic acid probes of an appropriate length are prepared based on a consideration of the sequence, e.g., as shown SEQ ID NO:1 and SEQ ID NO:2 or derived from flanking regions of these genes. The ability of such nucleic acid probes to specifically hybridize to the *S. typhimurium* gene sequences lend them particular utility in a variety of embodiments. The probes can be used in a variety of diagnostic assays for detecting the presence of pathogenic organisms in a given sample. However, other uses are envisioned, including the use of the sequence information for the preparation of mutant species primers, or primers for use in preparing other genetic constructs.

To provide certain of the advantages in accordance with the invention, the preferred nucleic acid sequence employed for hybridizations or assays includes sequences that are complementary to at least a 10 to 40, or so, nucleotide stretch of the selected sequence, such as that shown in FIG. 1 or FIG. 2, SEQ ID NO:1 or SEQ ID NO:2. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

Accordingly, the nucleotide sequences of the invention are important for their ability to selectively form duplex molecules with complementary stretches of *S. typhimurium* gene segments. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02 M-0.15 M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15 M-0.9 M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

The present invention is envisioned as useful in the cloning of nucleic acids encoding certain exportation polypeptides. Identification of other exportation polypeptides in addition to the 46 kDa and 55 kDa proteins should be possible using methods analogous to those disclosed herein. One method would be to produce a cDNA library using mRNA obtained from mutant *S. typhimurium* strains. Although the production of cDNA libraries from bacteria is not commonly done because of the usual absence of poly-A tails on prokaryotic messages, a cDNA library could be constructed from *S. typhimurium* mRNA.

A method of preparing variants of the *S. typhimurium* exportation polypeptides is site-directed mutagenesis. This technique is useful in the preparation of individual peptides, or biologically functional equivalent proteins or peptides, derived from the 46 kDa or 55 kDa protein sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art.

In general, site-directed mutagenesis in accordance herewith is performed by first obtaining a single-stranded vector which includes within its sequence a DNA sequence which encodes an export polypeptide. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence.

The preparation of sequence variants of the selected exportation polypeptide gene using site-directed mutagenesis is provided as a means of producing potentially useful exportation species and is not meant to be limiting as there are other ways in which sequence variants of the exportation polypeptide gene may be obtained. For example, recombinant vectors encoding the desired gene may be treated with mutagenic agents to obtain sequence variants (see, e.g., a method described by Eichenlaub, (1979) for the mutagenesis of plasmid DNA using hydroxylamine).

Isolation of Salmonella DNA segments was accomplished by isolation of DNA fragments containing the phoA gene fusions. TnphoA is a derivative of Tn5 which encodes *E. coli* alkaline phosphatase, minus the signal sequence and expression signals, inserted into the left IS50L element. Random transposition of TnphoA results in an active insertion only when the phoA gene sequence is fused inframe downstream of the promoter and export signals of a target gene A, FIG. 1. Plasmids containing phoA gene fusions can then be used as exposition vectors, FIG. 1, (B). The SSP1 and the PvuII restriction sites in phoA are blunt ended sites at which inframe insertions (IF) of a gene of interest (GOI) can be inserted. The resulting tribrid gene fusions, shown as C in FIG. 1, contain the expression and export signals of the target gene fused inframe with the phoA and GOI sequences.

FIG. 1 is a schematic representation of typical phoA fusions and illustrating cloning of successful fusions. The point at which the phoA sequence joins the target gene is referred to as the fusion joint (FJ). The remaining portion of the gene begins at the distal joint (DJ). Utilizing restriction enzymes which cut either downstream of the kanamycin resistance gene (e.g., BamHI) or the phoA gene sequence (e.g., HindIII) allows cloning of phoA gene fusions, provided the target gene is not cleaved ("R"). The fusion joint, including all the phoA gene fusions and upstream Salmonella sequences, were cloned into the HindIII or BamHI site of pBR322, FIGS. 2 and 3. Plasmids containing phoA gene fusions were then used as exposition vectors. Cells produced fusion polypeptides that had alkaline phosphatase activity, indicated by the formation of blue colonies on agar supplemented with the indicator dye (5-bromo-4-chloro-3-indolylphosphate).

The following examples are intended to illustrate the practice of the present invention and are not intended to be limiting. Although the invention is demonstrated with nucleic acid segments isolated from a strain of Salmonella, similar functions may be obtained from nucleic acid segments from other Salmonella strains and even other microorganisms. The nucleic acid sequences identified and the corresponding encoded polypeptides are useful in developing methods of producing a wide variety of heterologous proteins as well as expression vectors for localizing polypeptides in selected areas of a host cell.

EXAMPLE 1

Figure 3:
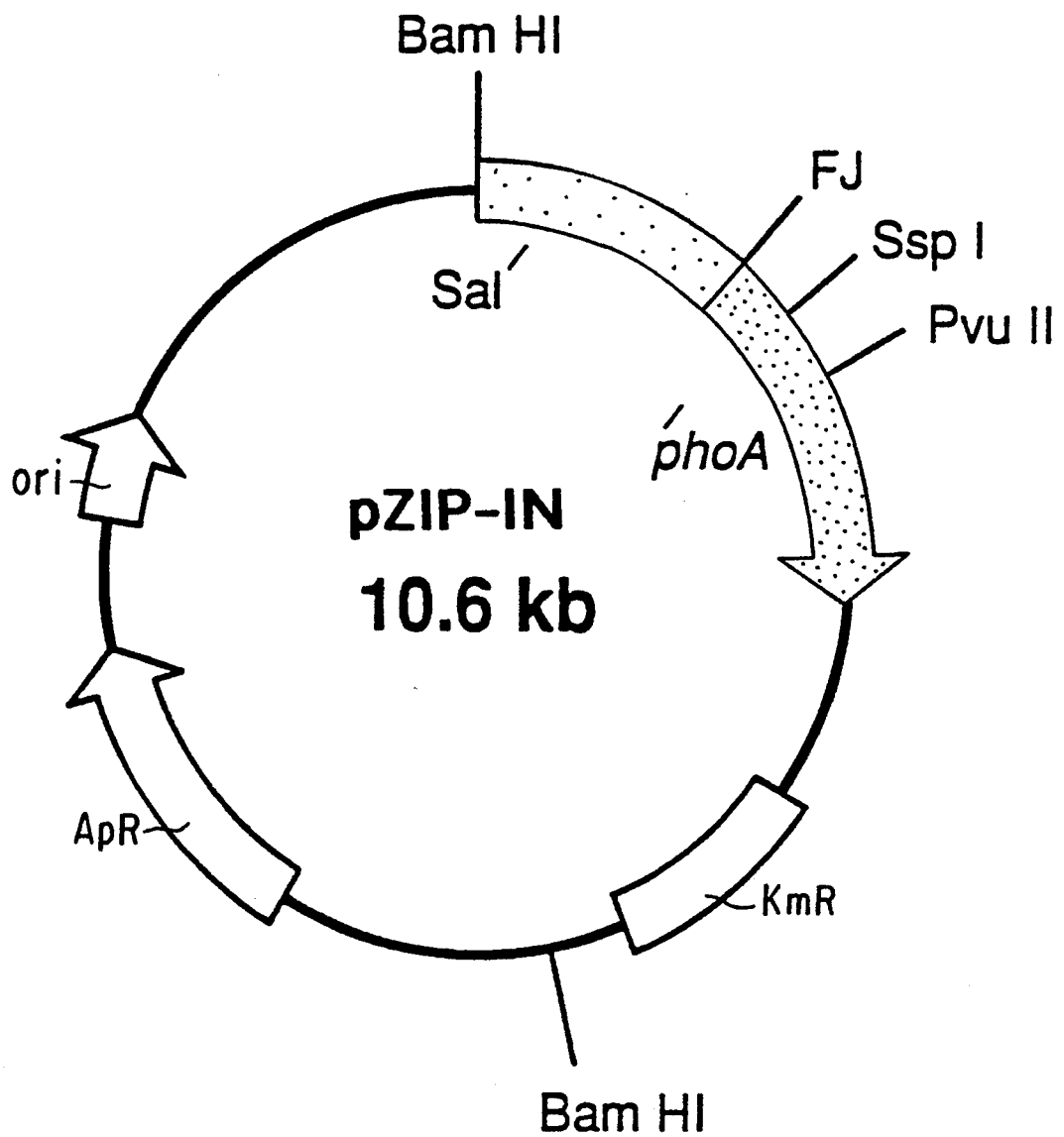
FIG. 3 shows plasmid pSIP-IN which contains a BamHI chromosomal fragment from *S. typhimurium* TnphoA insertion mutant TAG 28, inserted into pBR322 at the BamHI site. It expresses a 55 kd PhoA fusion protein which localizes to the inner membrane.

The following illustrates construction of plasmid pZIP-IN (FIG. 3). This plasmid contains a chimeric gene including a DNA segment from a strain of Salmonella fused with a segment of the alkaline phosphatase gene lacking signal and expression sequences. When expressed in a suitable host cell, the fusion product is localized to the inner membrane/periplasmic space of the host cell.

Preparation of p-ZIP-IN pZIP-IN, FIG. 3, is a derivative of pBR322 containing a BamHI fragment encoding alkaline phosphatase activity and kanamycin resistance inserted at the BamHI site. The BamHI fragment was cloned from a chromosomal DNA preparation of the TnphoA insertion mutant TAG28, which was constructed by TnphoA mutagenesis (see above) of *S. typhimurium* TA2361 (phoN mutant derived from LT2).

Chromosomal DNA was prepared from 50 ml of overnight growth of TAG28 in L-broth with vigorous shaking at 37° C. The bacterial culture was precipitated and washed once in phosphate buffered saline (pH 7.0). The washed bacterial pellet was resuspended in 10 ml of ice cold ET buffer [10 mM EDTA, 10 mM Tris-HCl (pH 8.0)]. Lysozyme was added to a concentration of 0.1 mg/ml and incubated for 15 minutes at 37° C. 1.2 ml of sarkosyl-pronase solution (10% sarkosyl, 5 mg/ml pronase in ET buffer) was added and the solution was incubated for 1 hr at 37° C. The solution was then extracted 3 times with TE [(10 mM Tris HCl, 1 mM EDTA (pH 8.0)]saturated phenol followed by 3 extractions with chloroform:isoamyl alcohol (24:1). The aqueous phase was transferred to a 50 ml beaker on ice and one-half volume of 7.5 M ammonium acetate was added. Three volumes of ice cold absolute ethanol was gently layered on top of the solution. The chromosomal DNA was precipitated onto a glass rod by gently stirring the solution to mix the interface. The precipitated DNA was rinsed once in 70% ice cold ethanol and dissolved overnight in 2 ml of TE buffer at 4° C. The concentration of DNA was quantitated by measuring the O.D. at 260 nm.

2 μg of TAG 28 chromosomal DNA was digested with BamHI at 37° C. for 2 hrs. The solution was extracted once with TE saturated phenol, followed by 2 extractions with chloroform:isoamyl alcohol (24:1). The aqueous phase was removed and the DNA precipitated by the addition of 1/10 volume 3 M sodium acetate (pH 5.2) and 2 volumes of ethanol followed by centrifugation in a microcentrifuge. 0.2 μg of pBR322 DNA was digested with BamHI and prepared for ligation as above. Ligation of the vector DNA (pBR322) and TAG 28 chromosomal DNA was performed by overnight incubation at 4° C. in 20 μl of 1× commercial (Promega) ligase buffer and 2 U of T4 DNA ligase.

pZIP-IN was isolated from the ligation reaction by transformation of subcloning efficiency DH5α competent cells. 5 μl of the ligation mixture was added to 50 μl of DH5α competent cells and incubated on ice for 30 minutes. Cells were heat shocked for 30 seconds by incubating in a 37° C. water bath. Cells were cooled on ice for 2 minutes and 0.950 ml of L-Broth was added to the tube. Cells were incubated for 1 hr at 37° C. Transformants with alkaline phosphatase activity and kanamycin resistance were selected by plating 0.1 ml of the bacterial culture on the L-agar plates containing 50 μg/ml kanamycin and 40 μg/ml BCIP (5-bromo-4-chloro-3-indolyl phosphate), followed by overnight incubation at 37° C. The following day, kanamycin resistant colonies were visible and all were blue, indicating the transformants had alkaline phosphatase activity. This was confirmed by alkaline phosphatase assays, Western blotting with monoclonal antibodies to alkaline phosphatase, and DNA sequencing of the fusion joint. FIG. 3 shows a partial restriction map of pZIP-IN.

EXAMPLE

The following example illustrates the construction of pZIP-OUT, FIG. 2. The plasmid is constructed from a DNA segment of Salmonella and a PhoA DNA segment lacking signal and expression sequences. When expressed from a suitable host cell, the fusion protein is localized to the outer membrane of the host cell.

Construction of pZIP-OUT

Genomic DNA was isolated from strain TAP43. A 25 ml culture in LB broth was grown overnight at 37° C. with shaking. The cells were harvested by centrifugation, and the pellet washed once in PBS. The washed pellet was resuspended in 10 mls of cold TE buffer (10 mM Tris-HCl, pH 8.0, 1 mM EDTA). One ml of a 1 mg/ml lysozyme solution was added, and the mixture was incubated in a 37° C. water bath for fifteen minutes. After this incubation, 1.2 ml of 10% sarkosyl, 5 mg/ml pronase in TE buffer was added, and incubation continued at 37° C. for 1-2 hours, until cell lysis occurred. The lysate was then extracted twice with an equal volume of phenol, once with phenol/chloroform, and once with chloroform. To the final extraction, a half-volume of 7.5 M ammonium acetate was added. The solution was mixed gently and placed on ice. Two volumes of ice-cold absolute ethanol were layered on top of the lysate, and the chromosomal DNA was collected at the interface by spooling on a glass rod. The spooled DNA was rinsed once in 70% ethanol, and then allowed to dissolve off of the glass rod into TE buffer overnight at 4°. The buffer, containing the dissolved DNA, was then ethanol-precipitated. The purified chromosome was collected by centrifugation and resuspended in a small volume of TE buffer. 1-5 μg of the purified DNA was restricted with HindIII, and then phenol/chloroform extracted and ethanol precipitated. The sample was collected by centrifugation, the pellet washed once with 70% ethanol, and dried under vacuum.

Vector pUC18 was also restricted with HindII, extracted, and precipitated in the same manner. The HindIII fragments of the genomic DNA were then ligated into the HindIII site of pUC18 with T4 DNA ligase. After ligation, the DNA was transformed into competent DH5α cells and plated on L-agar supplemented with ampicillin and BCIP (5-bromo-4-chloro-3-indolyl phosphate), both at 40 μg/ml. Blue colonies, indicating the presence of an active alkaline phosphatase fusion in the transformant, were selected and analyzed by restriction mapping. Transformant 43-17 contained a 4.5 kbp HindIII insert in the pUC18 vector. 3.1 kbp of this insert consisted of phoA sequences, with the remaining 1.4 kbp being derived from Salmonella chromosomal sequences.

Figure 4:
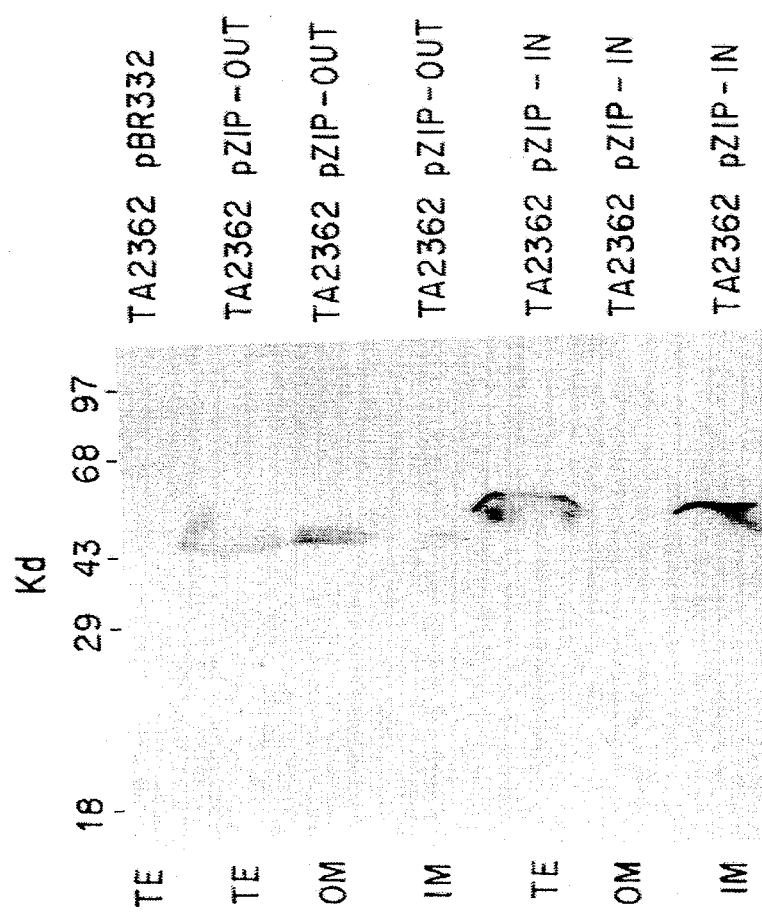
FIG. 4 is an immunoblot analysis of Salmonella membrane preparations using mouse anti-alkaline phosphatase. *S. typhimurium* TA 2362 harboring pBR322 showed no reaction in the total envelope (TE). TA 2362 harboring pZIP-OUT showed a 46 Kd PHOA fusion in the TE and after separation of the inner and outer membrane by treatment with 0.5% sarkosyl, the majority of the fusion protein was associated with the outer membrane (OM). TA 2362 harboring pZIP-IN showed a 55 Kd PhoA fusion protein in the TE and after separation of the inner and outer membrane by treatment with 0.5% sarkosyl, the majority of the fusion protein was found associated with the inner membrane (IM). All lanes were loaded with membrane preparations from an equal amount of cells.

The identity of this clone as a phoA fusion was confirmed not only by restriction analysis, but also by Southern blotting, FIG. 4 and sequencing. The Salmonella-phoA fusion contained within this HindIII fragment was designated as the pZIP-OUT cassette. This cassette was subsequently cloned into the HindIII sites of the vectors pBR322 and pAT153. The general structure of pZIP-OUT is shown in FIG. 2.

EXAMPLE 3

The following example illustrates how DNA may be fused to the gene segments of plasmid pZIP-IN, shown in this example with a portion of the cholera subunit B gene.

Construction of pIMB13 pIMB13 is a derivative of pZIP-IN in which the final 294 base pairs of ctxB have been inserted in frame with the phoA gene sequence at the SspI site. The inserted fragment containing the ctxB gene sequence is from pRIT10810 which encodes the entire ctxB gene. First, the SspI site in the pBR322 portion of pZIP-IN was eliminated as follows 2 μg of a plasmid preparation of pZIP-IN was digested with ScaI and EcoRV. Both enzymes cut at a single site within the pBR322 portion of the vector and generate compatible blunt ends. The digested DNA was precipitated and ligation was performed in 20 μl of 1× ligase buffer containing 1 U of T4 DNA ligase overnight at 4° C. DH5α frozen competent cells were transformed with 5 μl of the ligation reaction mixture.

Transformants were selected on L-agar plates containing 50 μg/ml kanamycin. Colonies were then replicated to L-agar plates containing 40 μg/ml ampicillin. Loss of ampicillin resistance encoded by pZIP-IN indicated that the segment from ScaI (3844) to EcoRV (185) which contained the SspI site (4168) had been eliminated. The resulting plasmid pΔS28-1 contained a single SspI site in the phoA sequence which generates an in-frame blunt end cut.

pIMB13 was constructed from pΔS28-1 as follows. The ctxB sequence encoded by pRIT10810 contains an SspI site which generates an in-frame blunt end cut near the 5′ end of the structural gene. pRIT1080 also contains an SspI site in the pBR322 portion of the vector. Digestion of pRIT101810 with SspI generates 2 fragments, one of which contains the 3′ final 294 base pairs of ctxB. 2 μg of pΔS28-1 and 2 μg of pRIT10810 were digested with SspI. Following phenol/chloroform extraction, the samples were combined and precipitated with 2 volumes of ethanol. Ligation of the sample was performed in 20 μl of 1× ligase buffer containing 1 U T4 DNA ligase. DH5α frozen competent cells were transformed with 5 μl of the ligation mixture. Transformants were selected on L-agar plates containing 50 μg/ml kanamycin and 40 μg/ml BCIP. Colonies harboring pΔS28-1 with inserts at the phoA SspI site appeared white since insertion interrupted the active phoA gene fusion. White kanamycin resistant colonies were picked for isolation and screened for expression of a ctxB fusion protein by Western blotting of total envelope fractions with affinity purified anti-ctxB. A DH5α strain harboring a derivative of pZIP-IN encoding a ctxB gene fusion was identified and the plasmid was designated pIMB13.

EXAMPLE 4

The following example is an example of a tripartite fusion prepared from plasmid pZIP-OUT. This plasmid may be used to express a fusion polypeptide from suitable host cells. The DNA inserted in this example is a segment from cholera B toxin subunit.

Construction of pRSP18

The construction of the trihybrid fusion, pRSP18, was accomplished as follows. Plasmid pRIT10810, containing the cholera toxin B gene, was first restricted with EcoRI and PstI. The ends generated by these restrictions were repaired with Klenow, and the vector was ligated back together. This created a 0.8 kbp deletion in pRIT10810, eliminating an undesirable SspI site in the vector. This deleted pRIT10810 was then restricted with HindIII and SspI. pZIP-OUT (in vector pUC18) was doubly restricted with HindIII and PvuII. A 2.0 kbp fragment generated from this double restriction, consisting of 1.4 kbp of Salmonella sequence and 0.6 kbp of phoA, was isolated and purified after agarose gel electrophoresis. This 2.0 kbp fragment was then unidirectionally ligated into the HindIII/SspI digested pRIT10810. This generated an in-frame fusion of the Salmonella-phoA sequences to the ctxB sequence (pSP-18). This clone was selected for on the basis of weak tetracycline resistance (1 µg/ml in L-agar). To make further manipulations of the plasmid more efficient, a kanamycin gene block (Pharmacia) was cloned into the BamHI site of PSP18, resulting in the plasmid construction pRSP18.

EXAMPLE 5

This example illustrates the procedure for extracting and separating bacterial membranes. After isolation of the membrane fragments, they were analyzed for localization of fusion peptides.

Preparation of Bacterial Membranes (Total Envelope) and Separation into Inner and Outer Membrane Fractions 100 ml of overnight bacterial cultures grown in L-Broth with vigorous shaking were pelleted and washed 1× in phosphate buffered saline (pH 7.0). Washed pellets were resuspended in 3 ml of membrane isolation buffer [10 mM $NaPO_4$, 0.5 mM $MgSO_4$ (pH 7.0)]. Samples were sonicated for 20 seconds 3 times with cooling on ice in between. Unbroken cells were removed by centrifugation at 7,000 rpm in a Beckman ultracentrifuge SW55 rotor for 1 hr. The supernatants were removed and total envelope pellets were rinsed 1× in sterile deionized water. Pellets were resuspended in 40 µl of sterile deionized water. One-half (20 µl) was saved for Western analysis of the total envelope. A 5% solution of sarkosyl in sterile deionized water was added to the remaining 20 µl to a final concentration of 0.5%. The samples were incubated for 30 minutes at room temperature and centrifuged in a microcentrifuge to pellet the non-soluble fraction representing the outer membrane. The supernatant was removed for Western analysis of the inner membrane fraction. The outer membrane pellet was rinsed once in sterile deionized water and saved for Western analysis. FIG. 4 shows immunoblot analysis of membrane preparations using mouse anti-alkaline phosphatase.

EXAMPLE 6

The following example describes the analysis of alkaline phosphatase activity. For the purposes of the present invention, alkaline phosphatase assays were performed to test for enzyme activity in membrane fractions of host cells in which alkaline fusion proteins were expressed.

Alkaline Phosphatase Assays

Alkaline phosphatase activity encoded by pZIP-IN and pZIP-OUT was confirmed by spectrophotometric assay using the chromogenic alkaline phosphatase substrate para-nitrophenol phosphate (PNPP). One ml of overnight bacterial cultures was pelleted for 15 seconds in a microcentrifuge. The pellet was washed once in 1 M Tris-HCl (pH 8.0) and resuspended in 1 ml of 1 M Tris-HCl (pH 8.0). The O.D. 600 of the bacterial suspension was recorded. 50 µl of chloroform and 50 µl of 0.1% SDS were added to permeabilize the cells. Samples were vortexed briefly. 0.1 ml of a 0.4% solution of PNPP in 1 M Tris-HCl (pH 8.0) was added and samples were incubated at 37° C. After significant yellow color was observed, 10 µl of 2.5 M $KPO_4$, 0.5 M EDTA was added and samples were placed on ice to stop the reaction. Cellular debris was removed by centrifugation in a microcentrifuge. O.D. 420 of the samples were recorded. The units of alkaline phosphatase activity were calculated by the following formula:

$$\text{Units activity} + 1{,}000 \times O.D.\ 420/\text{time of reaction} \\ (\text{minutes}) \times O.D.\ 600$$

Figure 5:
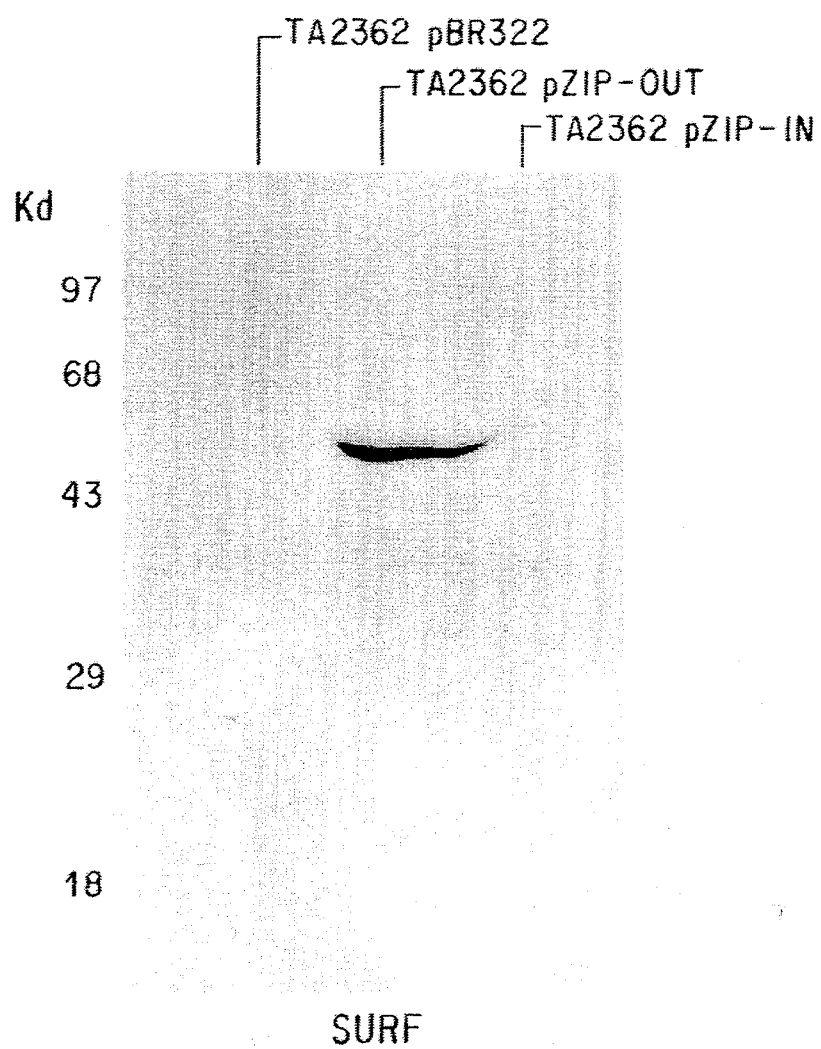
FIG. 5 is an immunoblot analysis of urea extracts (SURF) using anti-alkaline phosphatase as the primary antibody. *S. typhimurium* TA 2362 harboring pBR322 showed no reacting polypeptides to the alkaline phosphatase antibodies. TA 2362 harboring pZIP-OUT showed a PhoA fusion at 46 Kd. TA 2362 harboring pZIP-IN showed no reacting polypeptides with the same antisera. Lanes were loaded with an equivalent amount of extract prepared from an equivalent number of whole cells.

FIG. 5 shows an immunoblot analysis of urea extracts using anti-alkaline phosphatase as the primary antibody. No reaction is shown with plasmid pBR322 or with plasmid pZIP-IN. A reaction is shown with plasmid pZIP-OUT, indicating extraction of the alkaline phosphatase fusion protein.

EXAMPLE 7

The following outlines the general procedure for extracting proteins from bacterial cells.

Urea Extraction of Bacterial Cells

Ten ml of overnight stationary phase bacterial cultures grown in L-Broth with vigorous shaking were cooled on ice for 10 minutes and pelleted at 7,000 rpm in a Beckman J2-21 (JA-17 rotor). The bacterial pellet was washed 3 times in phosphate buffered saline (pH 7.0). The washed pellet was resuspended in 0.1 ml of 6 M urea containing 10 mM Tris-HCl (pH 7.5) and 5 mM EDTA. The suspension was incubated for 20 minutes on ice. Bacteria were pelleted in a microcentrifuge for 1 minute. Centrifugation of the supernatants was repeated to remove any traces of debris. Supernatants were frozen and 20 µl aliquots were used for SDS-PAGE and Western analysis.

EXAMPLE 8

The following example illustrates the expression of a ctxB polypeptide from an attenuated Salmonella strain with localization of the CtxB to the surface of the outer cell membrane.

Preparation of surface Expressed Cholera Toxin Subunit B

Figure 6:
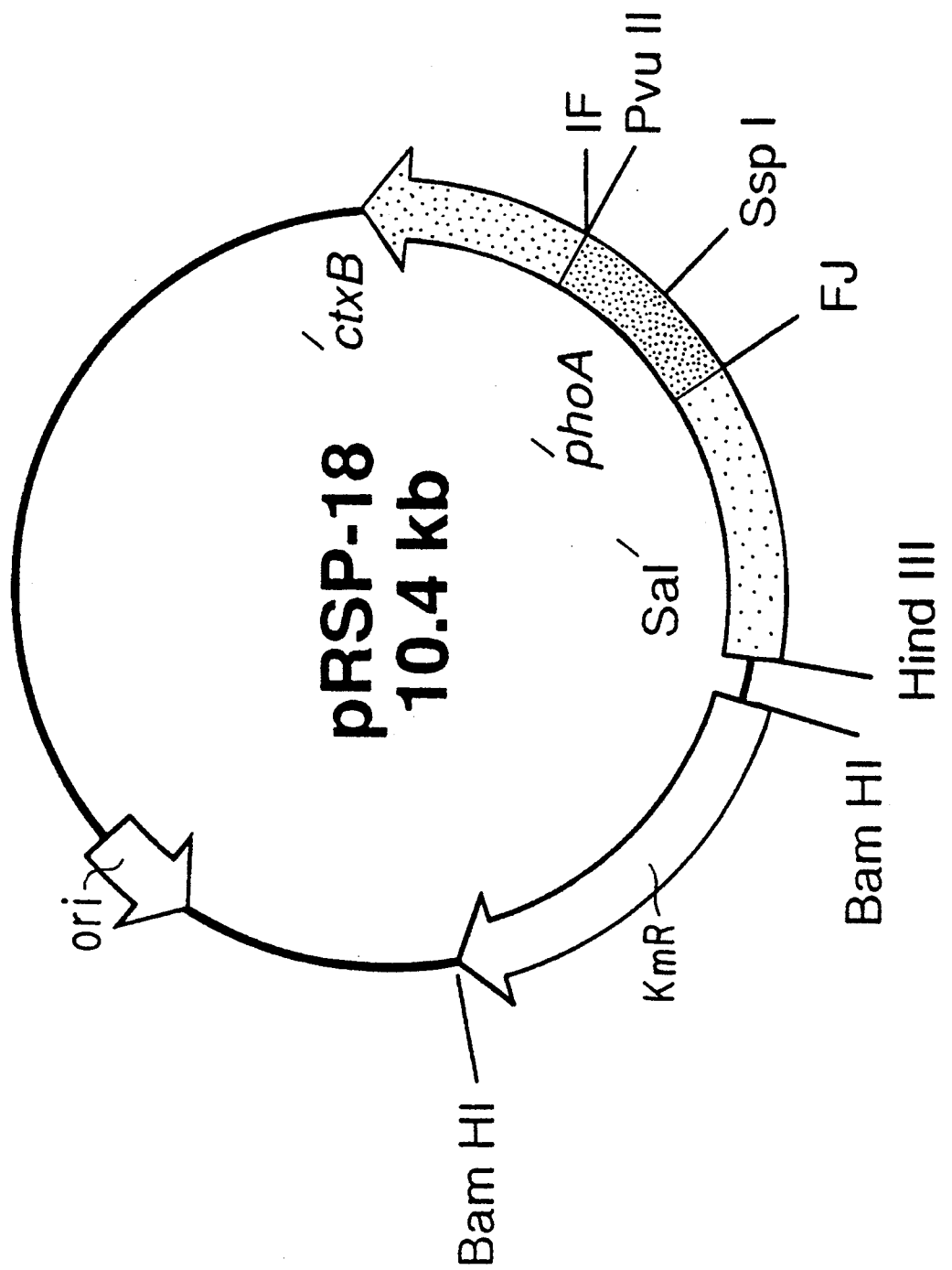
FIG. 6 shows the derivation of plasmid pRSP18 from pZIP-OUT in which the final 294 base pairs of ctxB have been inserted in frame (IF) with the phoA gene sequence at the PvuII site. The ctxB gene sequence is from pRIT10810 which encodes the entire ctxB gene (22).
Figure 7:
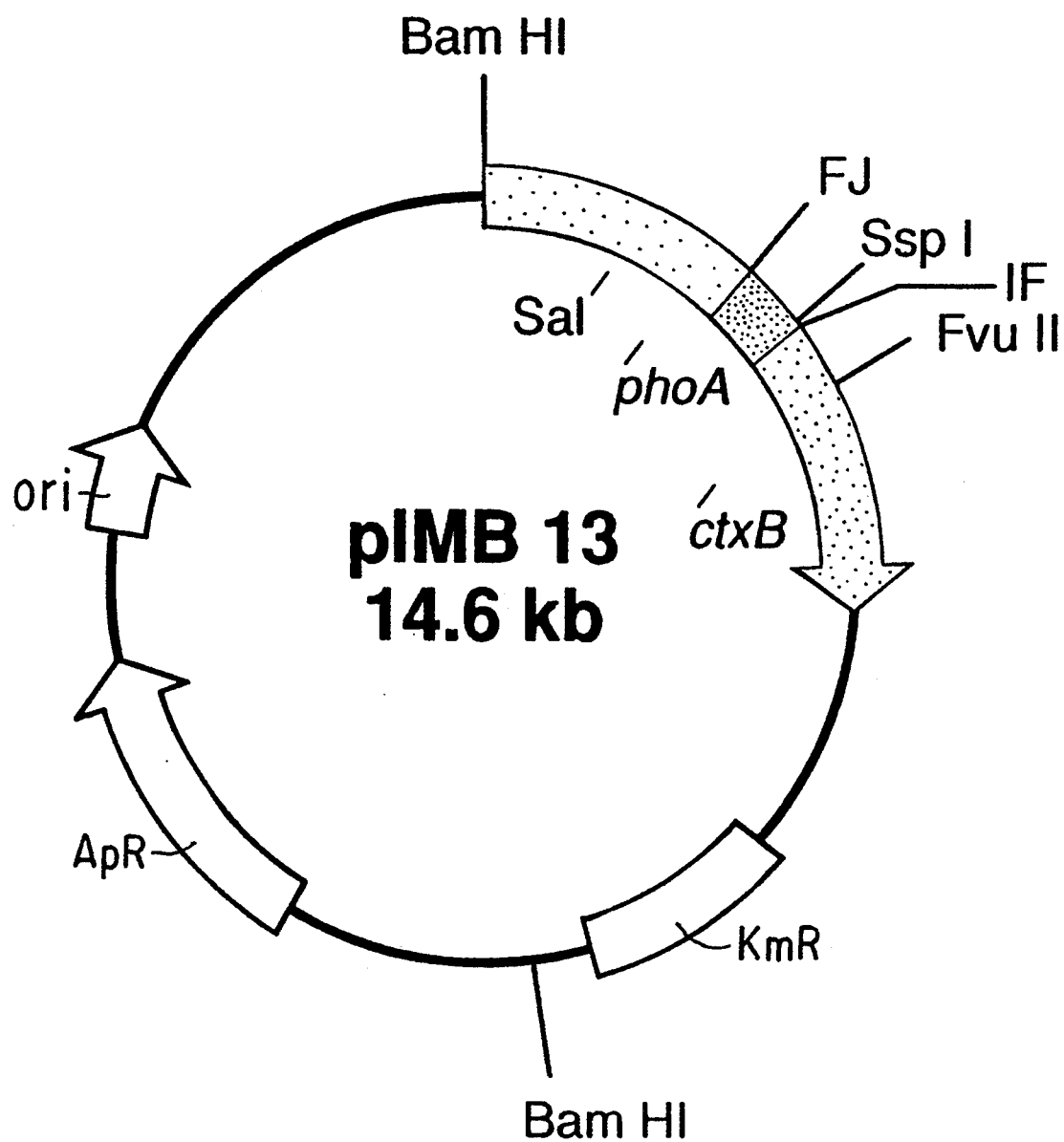
FIG. 7 shows the derivation of plasmid pIMB13 from pZIP-IN in which the final 294 base pairs of ctxB have been inserted in frame (IF) with the phoA gene sequence at the SspI site. The ctxB gene sequence is from pRIT10810 which encodes the entire ctxB gene (22).
Figure 8:
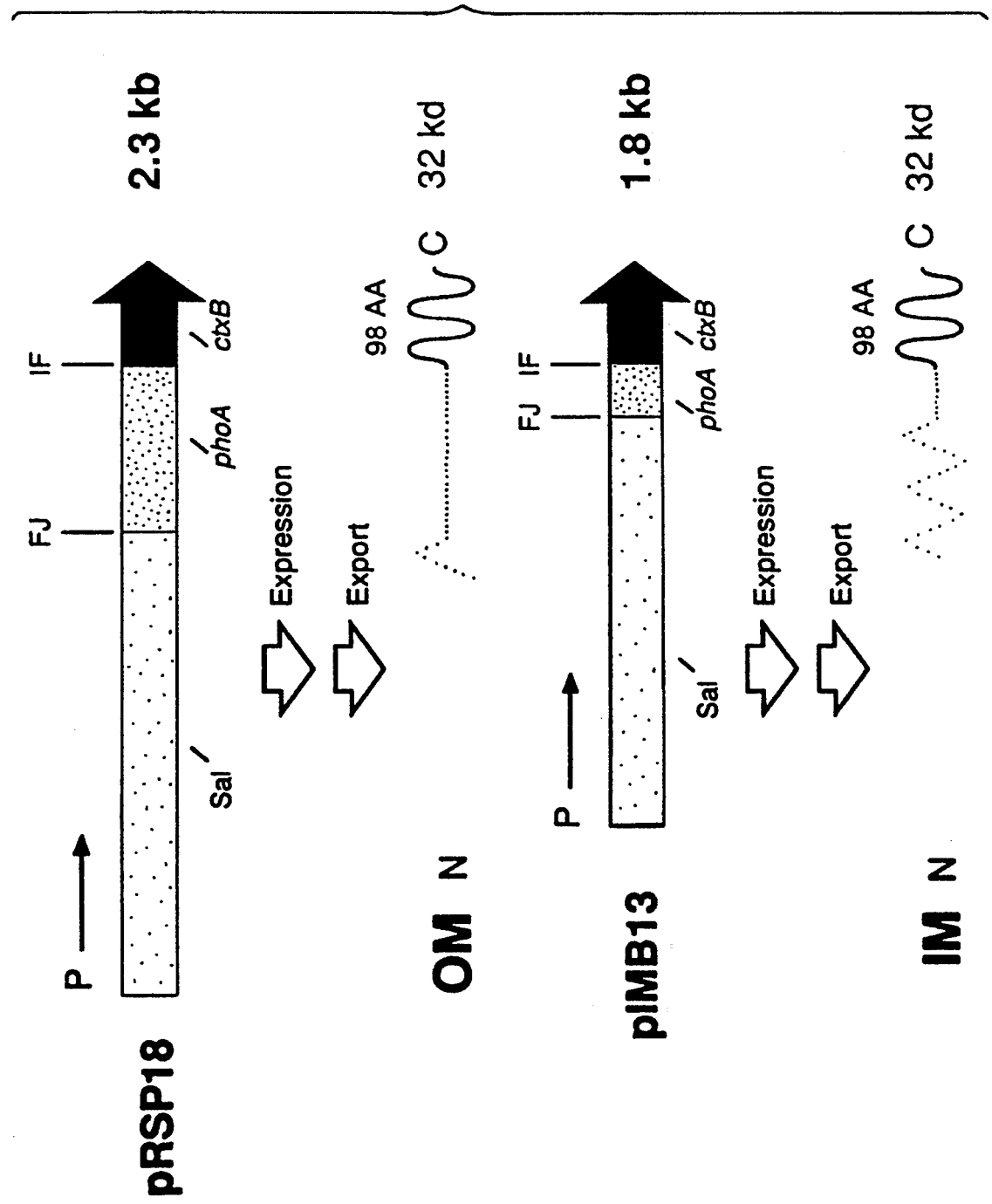
FIG. 8 is a schematic representation of the CtxB fusion from pRSP18 and pIMB13 that results in exportation of the 32 kDa CtxB protein to the outer and inner membranes, respectively.
Figure 9:
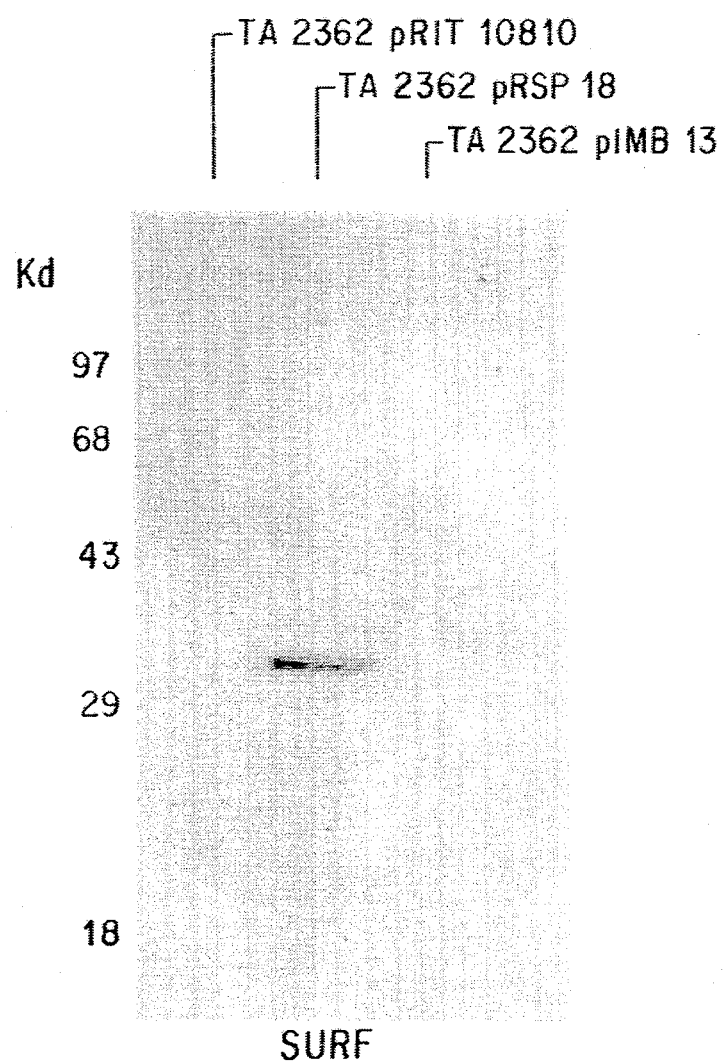
FIG. 9 is an immunoblot analysis of urea extracts (SURF) using affinity purified anti-CTB as the primary antibody. *S. typhimurium* TA 2362 harboring pRIT10810 which encodes cytoplasmically expressed CTB showed no reaction. TA 2362 harboring pRSP18 showed a CTB tribrid fusion protein at 32 Kd. TA 2362 harboring pIMB13 showed no reactivity to anti-CTB antibodies. Lanes were loaded with equal amounts of extract from equivalent numbers of whole cells.

The tribrid fusion in pRSP18 contains a 1.4 kb Salmonella DNA sequence which includes expression export signals, FIG. 6. The phoA sequence of the fusion includes approximately 0.6 kb from the phoA fusion joint (FJ) to the inframe insertion (IF) of ctxB. The ctxB sequence includes the final 294 base pairs of ctxB beginning at the inframe insertion site IF. Expression and export result in a 32 kDa tribrid fusion protein including the final 98 amino acids of ctxB at the C terminus which localizes to the outer membrane. The tribrid fusion in a pIMB13, FIG. 7, contains a 1.3 kb Salmonella DNA sequence which includes the expression and export signals of the expressed gene. The phoA sequence of the fusion includes approximately 0.2 kb from the phoA fusion joint FJ to the inframe insertion IF of ctxB. The ctxB sequence includes the final 294 base pairs of ctxB beginning at the inframe insertion site IF. Expression and export result in a 32 kDa tribrid fusion protein including the final 98 amino acids of ctxB at the C terminus which localizes to the inner membrane. FIG. 8 is a schematic representation of the fusion products.

Whole Salmonella TA2362 cells harboring pRSP18 were shown to express cholera B subunit on the outer surface membrane. Antisera to cholera toxin B subunit were prepared. Agglutination of TA2632 harboring pRSP18 was obtained. No agglutination was observed with strain TA2362 alone.

An immunoblot analysis of the membrane preparations was run using affinity urified rabbit anti-CTB. *S. typhimurium* TA 2362 harboring pRSP18 showed a 32 kDa CTB tribrid fusion protein in the total envelope (TE). Upon separation of the inner and outer membrane by treatment with 0.5% sarkosyl, the majority of the fusion protein was observed associated with the outer membrane (OM). TA 2362 harboring pIMB13 showed a 32 kDa CTB fusion protein in the total envelope (TE). Upon separation of the inner and outer membrane by treatment with 0.5% sarkosyl, the majority of the fusion protein was found associated with the inner membrane (IM). All lanes were loaded with membrane preparations prepared from an equivalent number of cells.

EXAMPLE 9

The following example illustrates the procedures contemplated as useful for creating an immune response in a mammal elicited with virulence attenuated Salmonella strains expressing antigens on the surface of the intact cell. In this example, CTB is used as an illustration.

Immunogenic Responses from Surface-Expressed CTB

All immune response experimentation will be conducted using CTB responding C57B/6 mice (15,16). An virulence attenuated *S. typhimurium* aroA phoN strain will be utilized in all experiments. Groups of 10 mice/condition will be challenged with the following: Salmonella alone, or Salmonella with cytoplasmically-encoded CTB (pRIT108010), or inner (pIMB-13, FIG. 7) or outer (pRSP-18, FIG. 6) membrane-expressed tribrid fusion encoding strains I. P. challenge ($5 \times 10^5$ cfu) and oral challenge ($5 \times 10^8$ cfu) will be evaluated. These challenge doses are expected to give optimal results but may require adjusting as necessary. Boosting will be 10 days post-challenge. Mucosal and serum anti-CTB levels will be determined after 1° and 2° challenge by ELISA (15,16) and by the ability to neutralize cholera toxin activity on adrenal cells (1). It will also be determined if the membrane-expressed CTB tribrid polypeptide retains its potent mucosal adjuvant activity (17) by comparing antibody titers to Salmonella and Salmonella expressing CTB. Since CTB mediates Ig class switching, we will also determine IgA/IgG ratios between the different challenge protocols by ELISA (17). Alternatively, the adjuvant activity of membrane expressed CTB will be evaluated using a purified antigen (i.e., ovalbumin) (18) for concurrent challenge with Salmonella or Salmonella expressing CTB strains. Additional experiments to further characterize adjuvant activity will be performed as indicated.

EXAMPLE 10

This example illustrates a contemplated method of inserting a fragment of HIV gp160 gene into plasmid pZIP-OUT of Example 2.

Construction of pZIP-OUT Encoding a 60 kDa Fragment of HIV gp120

A clone containing a 3.1 kb SalI- XhoI fragment encoding the HIV gp160 gene has been obtained. The coding regions of gp120 and gp41 are indicated by the arrow in FIG. 10. PvuII digestion of this fragment will yield a 1.8 kb fragment which deletes 0.7 kb of gp120 coding sequence. The 4.5 Kb pZIP-OUT cassette, bounded by HindIII sites, has been cloned into the HindIII site of vector pAT153 (ΔPvuII site). This construction has been designated pZIP-OUT-2. pZIP-OUT-2 will be digested with PvuII and SalI, and the PuvII - XhoI HIV fragment ligated into these sites. The tribrid fusion polypeptide predicted from this construction will yield a 82 kd polypeptide (2000–4000 dal, Salmonella: 20,000 dal, phoA: and 60,000 dal, Δgp120/gp41).

Figure 10:
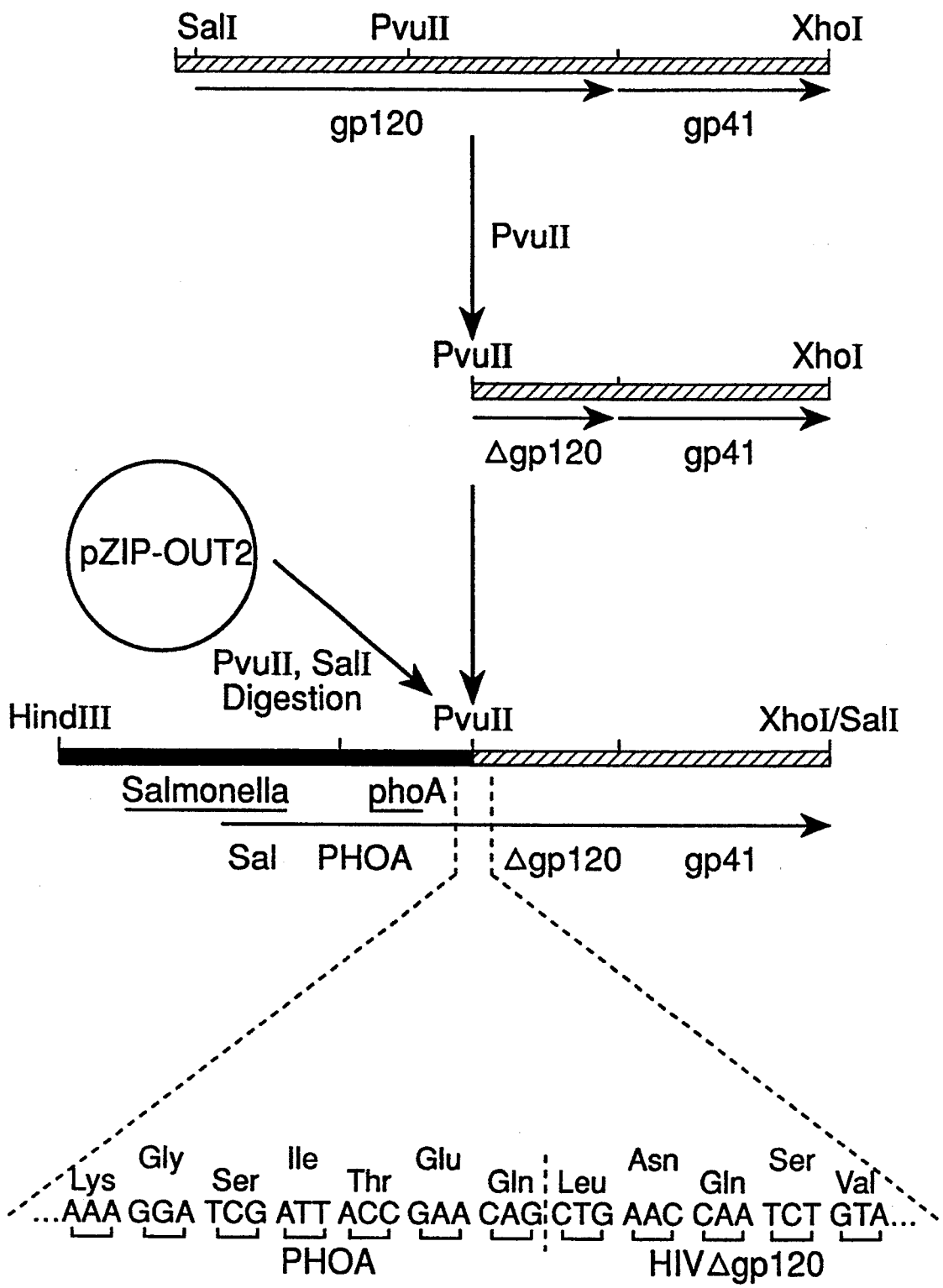
FIG. 10 is a proposed protocol for insertion of a fragment of HIV gp160 gene into pZIP-OUT. The nucleic acid sequence is SEQ ID NO:4 and the amino acid sequence is SEQ ID NO:5.

The predicted DNA sequence across the phoA fusion junction into gp120 is shown in FIG. 10. The phoA::gp120/gp41 reading frame is indicated by the brackets. The amino acid sequence across the fusion joint is shown.

EXAMPLE 11

The following outlines general protocols for sequencing.

Preparation of Templates pZIP-IN, pZIP-OUT, and pRSP18 were sequenced by the Sanger dideoxy protocol for double stranded DNA templates.

Purified plasmid preparations for sequencing were prepared as follows:
1. Each strain was grown overnight in 5 ml of LB broth (containing the appropriate antibiotic) at 37° C. with vigorous aeration.
2. The cultures were harvested by centrifugation. The cell pellets were resuspended in 100 μl of 50 mM glucose, 10 mM EDTA, and 25 mM Tris-HCl, pH 8.0, and incubated at room temperature for 5 minutes.
3. 200 μl of freshly prepared 0.2N NaOH, 1% SDS were added to each sample. The samples were mixed by inversion, and then incubated 5 minutes on ice.
4. 50 μl of 3 M potassium acetate (pH 4.8) were added to each sample. The samples were mixed by inversion and incubated for 5 minutes on ice.
5. The samples were then centrifuged for 5 minutes, and the supernatants transferred to fresh tubes. The samples were centrifuged a second time for 5 minutes and the supernatants transferred as before.

6. RNase A was added to a concentration of 20 μg/ml, and the samples were incubated at 37° C. for 20 minutes.
7. Each sample was phenol/chloroform extracted, chloroform extracted, and then ethanol-precipitated.
8. The DNA precipitates were collected by centrifugation and each DNA pellet was resuspended in 16 μl deionized water, 4 μl 4 M NaCl, and 20 μl 13% polyethylene glycol 8000. The samples were mixed well and incubated on ice for 20 minutes.
9. The samples were centrifuged 10 minutes and the supernatants discarded. The pellets were washed twice in 70% ethanol, dried, and resuspended in 20 μl of dH₂O.

Denaturation, Annealing, and Sequencing of Templates

For each DNA template prepared as above:

1. 2 μl of 2 M NaOH, 2 MM EDTA were added to the entire 20 μl sample and the sample was incubated for 10 minutes at room temperature.
2. The reactions were neutralized by the addition of 4.5 μl of 2 M sodium acetate (pH 5.0) and 5.5 μl of distilled H₂O. The samples were mixed well, and then precipitated with 100% ethanol.
3. The DNA pellets were collected by centrifuging for 15 minutes. The pellets were then washed once with 70% ethanol and dried.
4. All of the following reagents, except primers and radioactive label, were supplied in the Sequenase sequencing kit, United States Biochemical Co. The dried pellets were resuspended in 7 μl dH₂O, 2 μl of 5× Sequenase reaction buffer and 1 μl (~20 ng) of the appropriate primer. For sequencing the Salmonella sequences in pZIP-IN and pZIP-OUT, immediately upstream from the phoA junction, primer 1(AGA ATC ACG CAG AGC G) was used. For extended sequencing in the Salmonella sequences of pZIP-OUT, primer 2 (TTC AGG AAT GCA TGC) was utilized. To sequence across the phoA:ctxB junction in pRSP18, primer 3(AGC GCG ACC AGT GAA A) was used. The annealing reactions were incubated for 30 minutes at 37° C.
5. To each annealing mixture, 2 μl of 0.1M dithiothreitol, 2 μl of diluted labelling mix, 1 μl of [S³⁵]—dATP, and 2 μl of diluted Sequenase enzyme were added. The reactions were mixed and incubated at room temperature for 5 minutes.
6. 3.5 μl of each labelling reaction were then transferred to each termination mixture tube, containing dideoxy ATP, dideoxy GTP, dideoxy CTP, and dideoxy TTP. The chain termination reactions were allowed to proceed for 5 minutes at 37° C.
7. 4 μl of stop solution were added to each reaction, and the reactions were heated to 75° C. for 2-5 minutes.
8. The reactions were loaded onto a 6% acrylamide-urea sequencing gel and electrophoresed at 15 mA for 2-6 hours.
9. After electrophoresis, the sequencing gel was fixed in 10% methanol, 10% acetic acid, for 1 hour and then dried under vacuum for 1½ hours.
10. The dried gel was then exposed to autoradiograph film at room temperature for ~16 hours.

REFERENCES

The references listed below are incorporated herein by reference to the extent that they supplement, explain, provide a background for or teach methodology, techniques and/or compositions employed herein.

Sanchez, J., Johansson, S., Lowenadler, B., Svennerholm, A. M. and Holmgren, J., Res. Microbiol. 141, 971-979 (1990).

Strugnell, R. A., Maskell, D., Fairweather, N., Pickard, D., Cockayne, A., Penn, C. and dougan, G., Gene 88, 57-63 (1990).

Dougan, G., Hormaeche, C. E. and Maskell, D. J., Parasite Immunol. 9, 151-160 (1986).

Sory, M. -P. and Cornelis, G. R., Res. Microbiol. 141, 921-929 (1990).

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 221 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
AAATCCTGGA   AACCGATTCG   CCCCCTTATA   ACTATTGTCA   GATAACGTTC   TGACGGTTGT       60
GTAAAAACAT   GGCGCCTCAT   TCTTCTGTAG   TTGGAGTTAA   TATGAAAAAA   TTTTATAGCT      120
GTCTTCCTGT   CTTTTTACTG   ATCGGCTGTG   CTCCTGACTC   TTATACACAA   GTAGCGTCCT      180
GGACGGAACC   TTTCCCGTTT   TGCCCTGTTC   TGGAAAACCG   G                           221
```

( 2 ) INFORMATION FOR SEQ ID NO:2:

( i ) SEQUENCE CHARACTERISTICS:

(A) LENGTH: 377 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GCGTGCATAA TAAGCCCTAC ACAAATTGGG AGATATATCA TGAAAGGCTG GCTTTTTCTT      60

GTTATCGCAA TAGTTGGCGA AGTAATCGCA ACATCCGCAT TAAAATCTAG CGAGGGCTTT     120

ACTAAGCTTG CCCCTTCCGC CGTTGTCATA ATCGGTTATG GCATCGCATT TTATTTTCTT     180

TCTCTGGTTC TGAAATCCAT CCCTGTCGGT GTTGCTTATG CAGTCTGGTC GGGACTCGGC     240

GTCGTCATAA TTACAGCCAT TGCCTGGTTG CTTCATGGGC TGCGTGGGGC TTTGTAGGTA     300

TGGGGCTCAT AGCTGACTCT TATACACAAG ATGCGCCTGT GACGGAACCT TTCCCGTTTT     360

GCCCTGTTCT GGAAAAC                                                    377

(2) INFORMATION FOR SEQ ID NO:3:

(i) SEQUENCE CHARACTERISTICS:
            (A) LENGTH: 51 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:3:

Met  Ala  Pro  His  Ser  Ser  Val  Val  Gly  Val  Asn  Met  Lys  Lys  Phe  Tyr
    1              5                        10                            15

Ser  Cys  Leu  Pro  Val  Phe  Leu  Leu  Ile  Gly  Cys  Ala  Pro  Asp  Ser  Tyr
                  20                       25                       30

Thr  Gln  Val  Ala  Ser  Trp  Thr  Glu  Pro  Phe  Pro  Phe  Cys  Pro  Val  Leu
                  35                       40                       45

Glu  Asn  Arg
                  50

(2) INFORMATION FOR SEQ ID NO:4:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:4:

AAAGGATCGA TTACCGAACA GCTGAACCAA TCTGTA                                 36

(2) INFORMATION FOR SEQ ID NO:5:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Lys  Gly  Ser  Ile  Thr  Glu  Gln  Leu  Asn  Gln  Ser  Val
    1              5                        10

What is claimed is:

(a) SEQ ID NO:1;
(b) SEQ ID NO:2 ;
(c) DNA sequences complementary to (a) or (b); and
(d) Fragments of (a), (b) or (c) that encode an exportation polypeptide or fragments homologous to sequences encoding said polypeptide which localized to a *S. typhimurium* or *E. coli* cell membrane.

2. The DNA segment of claim 1 wherein the exportation polypeptide localizes a heterologous protein to said bacterial cell outer membrane.

3. The DNA segment of claim 1 which encodes an exportation polypeptide which localizes a heterologous protein to an inner membrane/periplasmic *S. typhimurium* or *E. coli* cell space.

4. A DNA which hybridizes to the DNA of (a) SEQ ID NO:1 , (b) SEQ ID NO:2, or DNA sequences complementary to (a) or (b) under high stringency conditions.

5. An isolated DNA fragment of (a) SEQ ID NO:1, (b) SEQ ID NO:2, or DNA sequences complementary to (a) or (b) that are between about 10 to about 30 base pairs and which will bind to genomic DNA encoding an exportation polypeptide that localizes to an *S. typhimurium* or *E. coli* membrane.

6. A DNA segment which corresponds to SEQ ID NO:1 encoding a 46 kDa polypeptide which localizes a heterologous protein to a *S. typhimurium* or *E. coli* bacterial cell outer membrane.

7. THE DNA segment of claim 6 wherein the 46 kDa polypeptide localizes the heterologoous peptide to the outer membrane external surface of the *S. typhimurium* or *E. coli* bacterial cell.

8. A DNA segment which corresponds to SEQ ID NO:2 encoding a 55 kDa exportation polypeptide which localizes a heterologous protein to a *S. typhimurium* or *E. coli* inner membrane/periplasmic space.

9. A recombinant cloning vector comprising the DNA segment of any one of claims 1, 4 or 5.

10. The recombinant vector of claim 9 wherein the DNA segment corresponds to SEQ ID NO:1 encoding an exportation polypeptide which localizes a heterologous protein to an outer membrena as a *S. typhimurium* or *E. coli* cell or to the external surface of the outer membrane.

11. The recombinant vector of claim 9 wherein the DNA segment corresponds to SEQ ID NO:2 encoding an exportation polypeptide which localizes a heterologoous protein to an inner membrane/cytoplasmic spaced of a *S. typhimurium* or *E. coli* bacterial cell.

12. The recombinant vector of claim 9 further comprising a gene encoding a desired polypeptide.

13. A *Salmonella typhimurium* cell transformed with the vector of claim 9.

14. The recombinant vector of claim 12 wherein the desired polypeptide comprises a detectable polypeptide.

15. The recombinant vector of claim 14 wherein the gene sequence encoding said polypeptide has a restriction site suitable for insertion of a DNA segment.

16. A method of obtaining a membrane-localized heterologous polypeptide comprising localizing a fusion protein to a *S. typhimurium* or *E. coli* cell membrane by transformation of the *S. typhimurium* or *E. coli* with the recombinant vector of claim 12 and culturing under conditions suitable for translation and expression of said polypeptide.

17. The method of claim 16 wherein the heterologous polypeptide comprises an antigenic protein or an epitode of said antigienic protein.

18. The method of claim 17 wherein the antigenic protein or epitope of said protein is cholera toxin subunit B.

19. A kit comprising at least one cloning vector in accordance with claim 9, the vector being suitably aliquoted into a container.

20. The kit of claim 19 comprising a first cloning vector encoding an exportation polypeptide which localizes to an inner membrane/cytoplasmic space of an *E. coli* or *S. typhimurium* host cell and a second cloning vector encoding an exportation polypeptide which localizes to outer membrane locations of said host cell.

21. The kit of claim 19 wherein the first cloning vector comprises PZIP-IN or pZIP-OUT.

22. The kit of claim 19 wherein the second cloning vector comprises pZIP-IN or pZIP-OUT.

23. The kit of claim 19 wherein the container is a test tube.

24. The kit of claim 19 wherein the vector is aliquoted in an amount suitable for convenient use.

* * * * *

UNITED STATES PATENT AND TRADEMARK OFFICE
CERTIFICATE OF CORRECTION

PATENT NO.   :   5,356,797

DATED        :   October 18, 1994

INVENTOR(S)  :   David W. Niesel, Scott Moncrief and Linda H. Phillips

It is certified that error appears in the above-identified patent and that said Letters Patent is hereby corrected as shown below:

In claim 1, column 27, line 1, insert --1. An isolated DNA containing a sequence encoding an exportation polypeptide which is selected from a group consisting of:-- therefor.

In claim 1, column 27, lines 6-7, delete "localized" and insert --localizes-- therefor.

In claim 10, column 27, line 43, delete "membrena" and insert --membrane-- therefor.

In claim 11, column 28, line 4, delete "heterologoous" and insert --heterologous-- therefor.

In claim 11, column 28, line 5, delete "spaced" and insert --space-- therefor.

In claim 17, column 28, lines 23-24, delete "epitode" and insert --epitope-- therefor.

UNITED STATES PATENT AND TRADEMARK OFFICE
CERTIFICATE OF CORRECTION

PATENT NO. : 5,356,797

DATED : October 18, 1994

INVENTOR(S) : David W. Niesel, Scott Moncrief and Linda H. Phillips

It is certified that error appears in the above-indentified patent and that said Letters Patent is hereby corrected as shown below:

In claim 17, column 28, line 24, delete "antigienic" and insert --antigenic-- therefor.

In claim 21, column 28, line 38, delete "PZIP-IN" and insert --pZIP-IN-- therefor.

Signed and Sealed this

Seventeenth Day of January, 1995

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,356,797                                Page 1 of 2
DATED     : October 18, 1994
INVENTOR(S) : David W. Niesel, et al.

It is certified that error appears in the above-indentified patent and that said Letters Patent is hereby corrected as shown below:

In column 4, lines 1 and 2, please delete "of FIG. 2" and substitute therefor --of FIG. 2A--.

In column 7, line 8, please delete "exposition" and substitute therefor --expression--.

In column 7, line 13, please insert --(C)-- after the phrase "tribid gene fusions".

In column 7, line 16, please delete "FIG. 2" and substitute therefor --FIG. 2B--.

In column 7, line 32, please delete "FIG. 2 also" and substitute therefor --FIG. 2A--.

In column 7, line 37, please delete "PHOA" and substitute therefor --PhoA--.

In column 13, line 45, please delete "FIG. 1 or FIG. 2,".

UNITED STATES PATENT AND TRADEMARK OFFICE
CERTIFICATE OF CORRECTION

PATENT NO. : 5,356,797
DATED : October 18, 1994
INVENTOR(S) : David W. Niesel, et al.

It is certified that error appears in the above-indentified patent and that said Letters Patent is hereby corrected as shown below:

In column 15, line 58, please delete "FIGS. 2 and 3" and substitute therefor --FIGS. 2A, 2B and 3"--.

In column 15, line 59, please delete "exposition" and substitute therefor --expression--.

Signed and Sealed this

Twenty-second Day of October, 1996

Attest:

BRUCE LEHMAN

Attesting Officer   Commissioner of Patents and Trademarks